US010729752B2

(12) United States Patent
Lowe et al.

(10) Patent No.: US 10,729,752 B2
(45) Date of Patent: Aug. 4, 2020

(54) COMPOSITIONS AND METHODS FOR TREATING CANCER WITH ARGININE DEPLETION AND IMMUNO ONCOLOGY AGENTS

(71) Applicant: AERASE, INC., Austin, TX (US)

(72) Inventors: David Lowe, Austin, TX (US); Scott W. Rowlinson, Austin, TX (US); Susan Alters, Palo Alto, CA (US); Giulia Agnello, Austin, TX (US)

(73) Assignee: AERASE, INC., Austin, TX (US)

( * ) Notice: Subject to any disclaimer, the term of this patent is extended or adjusted under 35 U.S.C. 154(b) by 60 days.

(21) Appl. No.: 15/699,951

(22) Filed: Sep. 8, 2017

(65) Prior Publication Data
US 2018/0177853 A1 Jun. 28, 2018

Related U.S. Application Data

(60) Provisional application No. 62/372,092, filed on Aug. 8, 2016, provisional application No. 62/524,286, filed on Jun. 23, 2017.

(51) Int. Cl.
*A61K 38/50* (2006.01)
*A61K 39/395* (2006.01)
*C07K 16/28* (2006.01)
*A61P 35/00* (2006.01)
*C07K 19/00* (2006.01)
*C12N 9/78* (2006.01)
*A61K 9/00* (2006.01)
*A61K 39/00* (2006.01)

(52) U.S. Cl.
CPC ............ *A61K 38/50* (2013.01); *A61K 9/0019* (2013.01); *A61K 39/3955* (2013.01); *A61P 35/00* (2018.01); *C07K 16/2818* (2013.01); *C07K 16/2827* (2013.01); *C07K 19/00* (2013.01); *C12N 9/78* (2013.01); *C12Y 305/03001* (2013.01); *A61K 2039/505* (2013.01)

(58) Field of Classification Search
None
See application file for complete search history.

(56) References Cited

U.S. PATENT DOCUMENTS

| 6,316,199 | B1 | 11/2001 | Vockley et al. |
|---|---|---|---|
| 8,398,968 | B2 | 3/2013 | Mayall |
| 8,440,184 | B2 | 5/2013 | Georgiou et al. |
| 9,050,340 | B2 | 6/2015 | Georgiou et al. |
| 10,098,933 | B2 | 10/2018 | Georgiou et al. |
| 2002/0119554 | A1 | 8/2002 | Vockley et al. |
| 2012/0177628 | A1 | 7/2012 | Georgiou et al. |
| 2014/0154797 | A1 | 6/2014 | Godfrin |
| 2014/0242060 | A1 | 8/2014 | Georgiou et al. |
| 2016/0095884 | A1 | 4/2016 | Godfrin et al. |
| 2017/0191078 | A1 | 7/2017 | Zhang et al. |
| 2017/0224843 | A1 | 8/2017 | Deglon et al. |
| 2017/0240922 | A1 | 8/2017 | Gill et al. |
| 2017/0283830 | A1 | 10/2017 | Saltzman et al. |
| 2018/0271960 | A1* | 9/2018 | Cheng ............ A61K 45/06 |

FOREIGN PATENT DOCUMENTS

| EP | 1803465 A1 | 7/2007 |
|---|---|---|
| JP | H02117383 A | 5/1990 |
| WO | 2003063780 A2 | 8/2003 |
| WO | 2004001048 A1 | 12/2003 |
| WO | 2012061015 A2 | 5/2012 |
| WO | 2015164743 A2 | 10/2015 |
| WO | 2016033555 A1 | 3/2016 |
| WO | WO-2018/032020 A1 | 2/2018 |

OTHER PUBLICATIONS

Lesterhuis et al (Scientific Reports, Jul. 2015, 5:12298).*
Ye et al (Journal of Immunology, 2016, 196:915-923; published online Dec. 9, 2015).*
Stone et al I (ACS Chemical Biology, 2010, 5:333-342).*
Stone et al II (Journal of Controlled Release, 2012, 158:171-179).*
Kelly et al (British Journal of Cancer, 2012, 106:324-332).*
Fletcher et al (American Asooc. Cancer Research, 2014, 75:275-283).*
Yu et al (Oncotarget, 2015, 6:42067-42079).*
Lopez et al., "Insights into the interaction of human arginase II with substrate and manganese ions by site-directed mutagnesis and kinetic studies. Alteration of substrate specificity by replacement of Asn149 with Asp", FEBS J. (2005): 272:4540-4548.
Lüneburg, N. et al., "Reference intervals for plasma L-arginine and the L-arginine: asymmetric dimethylarginine ratio in the Framingham Offspring Cohort", J. Nutr. (2011): 141(12): 2186-2190.
Marescau et al., "Guanidino compound analysis as a complementary diagnostic parameter for hyperargininemia, Follow-up guanidino compound levels during therapy", Pediatric. Res. (1990): 27(3): 297-303.
Marescau et al., "The pathobiochemistry of uremia and hyperargininemia further demonstrates a metabolic relationship between urea and guanidinosuccinic acid" (1992): 41(9): 1021-1024.
McGee et al., "Purification and characterization of Helicobacter pylori arginase, RocF: unique features among the arginase superfamily", Eur. J. Biochem. (2004): 271:1952-62.
Mora et al., "Implications of the S-shaped domain in the quaternary structure of human arginase", Biochemica Biophysica. Acta (2000): 1476: 181-90.
Ni et al., "Arginine deiminase, a potential anti-tumor drug", Cancer Lett. (2008): 261:1-11.
Oeffinger et al., "Outcome tools used for ambulatory children with cerebral palsy: responsiveness and minimum clinically important differences", Dev. Med. Chile Neurol. (2008): 50(12): 918-925.
Palacios et al., "Studies on the advent of ureotelism. The effects of bivalent cations on the capacity of the hepatic arginase of the Mexican axolotl to hydrolyse endogenous arginine", Biochem. J. (1969): 114(3):449-454.

(Continued)

*Primary Examiner* — Laura B Goddard
(74) *Attorney, Agent, or Firm* — Servilla Whitney LLC

(57) ABSTRACT

Methods of treating tumors or cancer include administration of an arginine depleting enzyme and an immune-oncology agent.

28 Claims, 7 Drawing Sheets

(56) References Cited

OTHER PUBLICATIONS

Periyannan et al., "Sequential binding of cobalt(II) to metallo-beta-lactamase CcrA", Biochemistry (2006): 45:1313-1320.
Prasad et al., "Argininemia: a treatable genetic cause of progressive spastic diplegia simulating cerebral palsy—case reports and literature review", J. Child Neurol. (1997): 12: 301-309.
Perrin, "421. The hydrolysis of manganese (II) ion", Journal of Chemistry Society (1962): 2197-2200.
Ratilla et al., "Terminal and new bridging coordination of methylguanidine, arginine, and canavanine to platinum (II). The first crystallographic study of bonding between a transition metal and a guanidine ligand", Inorganic Chemistry (1990): 29:918-926.
Reczkowski and Ash, "Rat liver arginase: kinetic mechanism, alternate substrates, and inhibitors", Arch. Biochem. Biophys. (1994): 312:31-7.
Rehner et al., "Effect of manganese cobalt and nickel on the activity of liver arginase in-vitro and in-vivo", Medizin und Emaehrung (1970): 11(2):32-35.
Robins and Shields, "Partial purification of bovine liver arginase", Archives of Biochemistry and Biophysics (1956): 62:55-62 (Abstract only).
Roopenian and Akilesh, "FcRn: the neonatal Fc receptor comes of age", Nat. Rev. Immunol. (2007): 7:715-725.
Sabio et al., "Glu-256 is a main structual determinant for oligomerisation of human arginase I", FEBS Lett. (2001): 501:161-165.
Santhanam et al., "Inducible NO synthase dependent S-nitrosylation and activation of arginase1 contribute to age-related endothelial dysfunction", Circ. Res. (2007): 101:692-702.
Sarkissian and Gámez, "Phenylalanine ammonia lyase, enzyme substitution therapy for phenylketonuria, where are we now?" Mol. Genet. Methab. (2005): 86(Suppl. 1): S22-6.
Savoca et al., "Cancer therapy with chemically modified enzymes. II. The therapeutic effectiveness of arginase, and arginase modified by the covalent attachment of polyethylene glycol, on the taper tumor and the L5178Y murine leukemia", Cancer Biochem. Biophys. ((984): 7:261-268.
Scolnick et al., "Altering the binuclear manganese cluster of arginase diminishes thermostability and catalytic function", Biochemistry (1997): 36:10558-10565.
Scott et al., "Single amino (arginine) deprivation: rapid and selective death of cultured transformed and malignant cells", Br. J. Cancer (2000): 83:800-10.
Schrover et al., "Minimal clinically important difference for the 6-min walk test: literature review and application to Morquio A syndrome", Orphanet. J. Rare Dis. (2017): 12(1):78.
Schlune et al., "Hyperargininemia due to arginase 1 deficiency: the original patients and their natural history, and a review of the literature", Amino Acids (2015): 47: 1751-1762.
Segawa et al., "A long-term survival case of arginase deficiency with severe multicystic white matter and compound mutations", Brain Dev. (2011): 33: 45-48.
Segel, Enzyme Kinetics: behavior and analysis of rapid equilibrium and steady state enzyme systems, New York, John Wiley and Sons, Inc., (1975): 914-917.
Shen et al., "Modulation of arginine metabolic pathways as the potential anti-tumor mechanism of recombinant arginine deiminase", Cancer Lett. (2006): 231:30-35.
Simmons et al., "Expression of full-length immunoglobulins in *Escherichia coli*: rapid and efficient production of aglycosylated antibodies", J. Immunol. Methods. (2002): 263:133-147.
Spector et al., "Properties of fetal and adult red blood cell arginase: a possible prenatal diagnostic test for arginase deficiency", Am. J. Hum. Genet. (1980): 32(1):79-87.
Stemmler et al., "EXAFS comparison of the dimanganese core structures of manganese catalase, arginase, and manganese-subsitituted ribonucleotide reductase and hemerythrin", Biochemistry. (1997): 36:9847-9858.

Stockler-Ipsiroglu et al., "Guanidinoacetate methyltransferase (GAMT) deficiency: outcomes in 48 individuals and recommendations for diagnosis, treatment and monitoring", Mol. Genet. Metab. (2014): 111(1): 16-25.
Stone et al., "Engineering human arginase I as a novel cancer therapeutic agent", retrieved from the Internet at http://aiche.conefx.com/aiche/09icbe/preliminaryprogram/abstract_143378.htm, retrieved on Feb. 29, 2012, dated Sep. 6, 2008.
Tao and Morrison, "Studies of aglycosylated chimeric mouse-human IgG. Role of carbohydrate in the structure and effector functions mediated by the human IgG constant region", J. Immunol. (1989): 143:2595-2601.
Uchino, T., et al., "Molecular basis of phenotypic variation in patients with argininemia", Hum. Genet. (1995): 96(3): 255-60.
Vockley et al., "Loss of functional mutations in conserved regions of the human arginase I gene", Biochemical and Molecular Medicine (1996): 59:44-51.
Wheatley and Campbell, "Arginine catabolism, liver extracts and cancer", Pathol. Oncol. Res. (2002): 8: 18-25.
Wheatley, "Arginine deprivation and metabolomics: important aspects of intermediary metabolism in relation to the differential sensitivity of normal and tumour cells", Semin. Cancer Biol. (2005): 15:247-253.
Wu, G. et al., "Arginine metabolism: nitric oxide and beyond", Biochem. J. (1998): 336 ( Pt 1), 1-17.
Yoon et al., "Renal cell carcinoma does not express argininosuccinate synthetase and is highly sensitive to arginine deprivation via arginine deiminase", Int. J. Cancer (2007): 120:897-905.
Examination Report dated Aug. 27, 2013 in EP Appl. No. 09824219.1.
Suppl. EP Search Report/Search Opinion dated May 31, 2012 in EP Appl. No. 09824219.1.
Examination Report dated Jun. 12, 2018 in EP Appl. No. 16163214.6.
Office Action dated Jun. 5, 2014 in JP Appl. No. 2011-534855.
International Search Report dated Jun. 17, 2010 in International Appl. No. PCT/US2009/062969.
International Search Report and Written Opinion dated Dec. 28, 2017 in International Appl. No. PCT/US17/50816.
Office Action dated Aug. 26, 2011 in U.S. Appl. No. 12/610,685.
Office Action dated Dec. 8, 2011 in U.S. Appl. No. 12/610,685.
Office Action dated May 24, 2012 in U.S. Appl. No. 12/610,685.
Office Action dated Feb. 24, 2014 in U.S. Appl. No. 13/863,448.
Office Action dated Jun. 19, 2014 in U.S. Appl. No. 13/863,448.
Office Action dated Aug. 22, 2013 in JP Appl. No. 2011-534855.
Ankudinov et al., "Real-space multiple-scattering calculation and interpretation of x-ray-absorption near-edge structure", Physical Review B (1998): 58:7565-7576.
Aoki et al., "Guanidine is a Zn(2+)-binding ligand at neutral pH in aqueous solution", J. Am. Chem. Soc., (2002): 124:5256-5257.
Ascierto et al., "Pegylated arginine deiminase treatment of patients with metastatic melanoma results from phase I and II studies", J. Clin. Oncol. (2005): 23:7660-7668.
Ash, "Structure and function of Arginases", The Journal of Nutrition (2004): 134:2760S-2764S.
"ATS Statement Guidelines for the Six-Minute Walk", Am. J. Respir. Crit. Care Med. (2002): 166: 111-117.
Auld and Vallee, "Kinetics of carboxypeptidase A. The pH dependence of tripeptide hydrolysis catalyzed by zinc, cobalt, and mahanese enzymes", Biochemistry (1970): 9:4352-4359.
Badarau and Page, "The variation of catalytic efficiency of Bacillus cereus metallo-beta-lactamase with different active site metal ions", Biochemistry, (2006): 45:10654-10666.
Bansal and Ochoa, "Arginine availability, arginase, and the immune response", Curr. Opin. Clin. Nutr. Metab. Care. (2003); 6:223-8.
Beale and Croft, "A sensitive method for the colorimetric determination of urea", J. Clin. Pathol. (1961): 14:418-24.
Bewley et al., "Crystal stuctures of Bacillus caldovelox arginase in complex with substrate and inhibitors reveal new insights into activation, inhibition and catalysis in the arginase superfamily", Structure (1999): 7:435-448.

(56) References Cited

OTHER PUBLICATIONS

Bickmore et al., "Bond-valence methods for pKa prediction. II. Bond-valence, electostatic, molecular geometry, and solvation effects", Geochimica et Cosmochimica Acta (2006): 70:4057-4071.
Burrage et al., "Human recombinant arginase enzyme reduces plasma arginine in mouse models of arginase deficiency", Hum. Mol. Genetics (2015): 24(22): 6417-27.
Cama et al., "Structure and functional importance of first-shell metal ligands in the binuclear manganese cluster of arginase I", Biochemistry (2003): 42:7748-7758.
Carvajal et al., "Consequences of mutations of metal ligands in human liver arginase I", Molecular Biology of the Cell (2002): 13: 546A.
Carvajal et al., "Interaction of arginase with metal ions: studies of the enzyme from human liver and comparison with other arginases", Comp. Biochem. Physiol. B. Biochem. Mol. Biol. (1995): 112:153-159.
Carvalho et al., "Clinical features and neurologic progression of hyperargininemia", Pediatr. Neurol. (2012): 46(6): 369-74.
Cavalli et al., "Mutagenesis of rat liver arginase expressed in Escherichia coli: role of conserved histidines", Biochemistry (1994): 33:10652-10657.
Chaberek et al., "Stability of metal chelates. II. β-hydroxyethyliminodiacetic acid", J. Am. Chem. Soc. (1952): 74:5057-60.
Cheng et al., "Enhanced hepatocyte growth factor signaling by type II transforming growth factor-beta receptor knockout fibroblasts promotes mammary tumorigenesis", Cancer Res. (2007): 67:4869-4877.
Cheng et al., "Pegylated recombinant human arginase (rhArg-peg5,000mw) inhibits the in vitro and in vivo proliferation of human hepatocellular carcinoma through arginine depletion", Cancer Res. (2007): 67:309-17.
Cheng et al., "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma", Cancer Lett. (2005): 224:67-80.
Christianson and Cox, "Catalysis by metal-activated hydroxide in zinc and manganese metalloenzymes", Annu. Rev. Biochem. (1999): 68:33-57.
Christianson and Fierke, "Carbonic anhydrase: evolution of the zinc binding site by nature and by design", Acc. Chem. Res. (1996): 29:331-339.
Colleluori et al., "Expression, purification, and characterization of human type II arginase", Arch. Biochem. Biophys. (2001): 389:135-143.
Deignan et al., "Increased plasma and tissue guanidine compounds in a mouse model of hyperargininemia", Mol. Genet. Metab. (2008): 93: 172-178.
Di Costanzo et al., "Stereochemistry of guanidine-metal interactions: implications for L-arginine-metal interactions in protein structure and function", Structure, Function, and Bioinformatics (2006): 65:637-42.
Dillon et al., "Biochemical characterization of the arginine degrading enzymes arginase and arginine deiminase and their effect on nitric oxide production", Med. Sci. Monit. (2002) 8:BR248-253.
Dowling et al., "Evolution of the arginase fold and functional diversity", Cell. Mol. Life Sci. (2008): 65:2039-55.
Downs et al., "The Berg Balance Scale", J. Physiother. (2015): 61(1):46.
Durante et al., "Arginase: a critical regulator of nitric oxide synthesis and vascular function", Clin. Exp. Pharmacol. Physiol. (2008): 34:906-911.
Enright et al., "Reference equations for the six-minute walk in healthy adults", Am. J. Respir. Crit. Care Med. (1998): 158(5 Pt 1): 1384-1387.
Ensor et al., "Pegylated arginine deiminase (ADI-SS PEG20,000 mw) inhibits human melanomas and hepatocellular carcinomas in vitro and in vivo", Cancer Res. (2002): 62:5443-5450.

Feun et al., "Clinical trial of CPT-11 and VM-26/VP-16 for patients with recurrent malignant brian tumors", J. Neurooncol. (2007): 82:177-181.
Geiger et al., "Six-minute walk test in children and adolescents", J. Pediatr. (2007): 150(4): 395-399.
Gill and von Hippel, "Calculation of protein extinction coefficients from amino acid sequence data", Anal. Biochem. (1989): 182:319-26.
Häberle et al., "Suggested guidelines for the diagnosis and management of urea cycle disorders", Orphanet. J. Rare Dis. (2012): 7: 32.
Han et al., "Synthesis and evaluation of alternative substrates for arginase", Bioorg Chem. (2002): 30:81-94.
Haraguchi et al., "Molecular cloning and nucleotide sequence of cDNA for human liver arginase", Proc. Natl. Acad. Sci. U.S.A. (1987): 84:412-415).
Harris et al., Clin. Pharmacokinet. (2001): 40(7): 539-51.
He et al., "Aminoguanidinium hydrolysis effected by a hydroxo-bridged dicobalt (II) complex as a functional model for arginase and catalyzed by mononuclear cobalt (II) complexes", J. Am. Chem. Soc. (1998): 120:105-113.
Irving and Williams, "Order of stability of metal complexes", Nature (1948): 162:746-747.
Izzo et al., "Pegylated arginine deiminase treatment of patients with unresectable hepatocellular carcinoma: results from I/II studies", J. Clin. Oncol. (2004): 22:1815-1822.
Jefferis, "Antibody therapeutics: isotype and glycoform selection", Expert. Opin. Biol. Ther. (2007): 7:1401-13.
Kalnine el al., Accession No. BT0199354, Synthetic construct Homo sapiens arginase, type II mRNA, partial cds, NCBI Protein DB[online], Oct. 28, 2004 [retrieved on Aug. 16, 2013], URL: http://www.ncbi.nlm.nih.gov/nuccore/BT019935.
Katusic, "Mechanisms of endothelial dysfunction induced by aging: Role of Arginase I", Circulation Research (2007): 101(7):640-641.
Khangulov et al., "L-arginine binding to liver arginase requires proton transfer to gateway residue His141 and coordination of the guanidinium group to the dimanganese(II,II) center", Biochemistry (1998): 37:8539-8550.
Knipp and Vasåk, "A colorimetric 96-well microtiter plate assay for the determination of enzymatically formed citrulline", Anal. Biochem. (2000): 268:257-64.
Kuhn et al., "pH-sensitive control of arginase by Mn(II) ions at submicromolar concentrations", Arch. Biochem. Biophys. (1991): 286:217-21.
Lambert et al., "Hyperargininemia: intellectual and motor improvement related to changes in biochemical data", J. Pediatr. (1991): 118(3): 420-4.
Lavulo et al., "Subunit-subunit interactions in trimeric arginase. Generation active monomers by mutation of a single amino acid", J. Biol. Chem. (2001): 276:14242-48.
The International Bureau of WIPO, International Preliminary Report on Patentability for International Patent Application No. PCT/US2017/050816 (Publication No. WO 2018/032020), dated Feb. 21, 2019.
Compaan, D., et al., "The Crystal Structure of the Costimulatory OX40-OX40L Complex," Structure, 2006, 14(8): 1321-1330.
Jeon, H., et al., "Structure and Cancer Immunotherapy of the B7 Family Member B7x," Cell Reports, 2014, 9(3): 1089-1098.
Linch, S., et al., "OX40 agonists and combination immunotherapy: putting the pedal to the metal," Frontiers in Oncology, 2015, 5: 34.
Vigdorovich, V., et al., "Structure and T Cell Inhibition Properties of B7 Family Member, B7-H3," Structure, 2013, 21(5): 707-717.
Zarganes-Tzitzikas, T., et al., "Inhibitors of programmed cell death 1 (PD-1): a patent review (2010-2015)," Expert Opinion on Therapeutic Patents, 2016, 26(9): 973-977.
Häberle, J., et al., "Suggested guidelines for the diagnosis and management of urea cycle disorders," Orphanet J. Rare Dis., 2012, 7: 32 (part 1 of 2, pp. 1-15).
Häberle, J., et al., "Suggested guidelines for the diagnosis and management of urea cycle disorders," Orphanet J. Rare Dis., 2012, 7: 32 (part 2 of 2, pp. 16-30).
Aeglea Biotherapeutics, Inc., "Aeglea BioTherapeutics to Present Topline Data from Phase 1 Trial of AEB1102 for Treatment of

(56) References Cited

OTHER PUBLICATIONS

Arginase I Deficiency at 2017 ACMG Annual Clinical Genetics Meeting," *Globe Newswire Press Release*, Mar. 23, 2017, available at: ir.aegleabio.com/news-releases/news-release-details/aeglea-biotherapeutics-present-topline-data-phase-1-trial.

* cited by examiner

COMPOSITIONS AND METHODS FOR TREATING CANCER WITH ARGININE DEPLETION AND IMMUNO ONCOLOGY AGENTS

CROSS-REFERENCE TO RELATED APPLICATIONS

This application claims priority to U.S. Application No. 62/372,092 filed on Aug. 8, 2016, and U.S. Application No. 62/524,286 filed on Jun. 23, 2017.

BACKGROUND OF THE INVENTION

It has been recognized for over 50 years that certain tumor cells have a high demand for amino acids, such as L-arginine and are killed under conditions of L-arginine depletion (Wheatley and Campbell, 2002). In human cells L-arginine is synthesized in three steps; first L-citrulline is synthesized from L-ornithine and carbamoyl phosphate by the enzyme ornithine transcarbamylase (OTC), argininosuccinate synthetase (ASS) converts L-citrulline and aspartate to argininosuccinate, followed by conversion of argininosuccinate to L-arginine and fumarate by argininosuccinate lyase (ASL). A large number of hepatocellular carcinomas (HCC), melanomas and, renal cell carcinomas (Ensor et al., 2002; Feun et al., 2007; Yoon et al., 2007) do not express ASS and thus are sensitive to L-arginine depletion. The molecular basis for the lack of ASS expression appears to be diverse and includes aberrant gene regulation. Whereas non-malignant cells enter into quiescence (Go) when depleted of L-arginine and thus remain viable for several weeks, tumor cells have cell cycle defects that lead to the re-initiation of DNA synthesis even though protein synthesis is inhibited, in turn resulting in major imbalances and rapid cell death (Shen et al., 2006; Scott et al., 2000). The selective toxicity of L-arginine depletion for HCC, melanoma and other ASS-deficient cancer cells has been extensively demonstrated in vitro, in xenograft animal models and in clinical trials (Ensor et al., 2002; Feun et al., 2007; Shen et al., 2006; Izzo et al., 2004). Recently Cheng et al. (2007) demonstrated that many HCC cells are also deficient in ornithine transcarbamylase expression and thus, they are also susceptible to enzymatic L-arginine depletion.

There is interest in the use of L-arginine hydrolytic enzymes for cancer therapy, especially the treatment of cancers such as hepatocarcinomas, melanomas and renal cell carcinomas, for example, which are common forms of cancer associated with high morbidity. Two L-arginine degrading enzymes have been used for cancer therapy: bacterial arginine deiminase and human arginases. Unfortunately, both of these enzymes display significant shortcomings that present major impediments to clinical use (immunogenicity, and low catalytic activity with very poor stability in serum, respectively). Thus, the therapeutic success of L-arginine depletion therapy will rely on addressing these shortcomings.

Another challenge in the treatment of many cancers is the ability of some cancers to evade the immune system. Some tumors, for example, do this through the immune checkpoint pathways, which are inhibitory pathways in the immune system that maintain self-tolerance by modulating immune response. These pathways can be dysregulated by tumors resulting in immune resistance. Some of these pathways, both agonists of prostimulatory receptors or antagonists of inhibitory signals, both of which result in amplification of antigen-specific T-cell responses, have become targets for cancer immunotherapy. Some exemplary receptors and ligands include cytotoxic T-lymphocyte-associated antigen 4 (CTLA4), programmed cell death 1 (PD1), programmed cell death ligand 1 (PDL1), lymphocyte activation gene 3 (LAG3), B7-H3, B-7-H4, and T cell membrane protein 3 (TIM3) among others. (Pardoll, 2012).

SUMMARY OF THE INVENTION

An aspect of the present disclosure generally relates to compositions and methods for the treatment of cancer with enzymes that deplete L-arginine in serum. In some embodiments, the cancer is one that does not express, or is otherwise deficient in, argininosuccinate synthetase (ASS), ornithine transcarbamylase (OTC), or argininosuccinate lyase (ASL).

In some aspects, the present invention also contemplates the use of arginase proteins wherein the natural metal cofactor ($Mn^{2+}$) is replaced with another metal. In particular embodiments, the arginase protein comprises an amino acid sequence of human Arginase I or an amino acid sequence of human Arginase II and a non-native metal cofactor. In some embodiments, the metal is cobalt ($Co^{2+}$). Human Arginase I and II proteins of the present invention have two Mn (II) sites; either or both sites can be substituted so as to generate a modified Arginase I or II protein with a non-native metal cofactor. In some embodiments, the protein displays a $k_{cat}/K_M$ greater than 400 $mM^{-1}$ $s^{-1}$ at pH 7.4. In a particular embodiment, the protein displays a $k_{cat}/K_M$ between 400 $mM^{-1}$ $s^{1}$ and 4,000 $mM^{-1}$ $s^{1}$ at pH 7.4. In another embodiment, the protein displays a $k_{cat}/K_M$ between 400 $mM^{-1}$ $s^{-1}$ and 2,500 $mM^{-1}$ $s^{-1}$ at pH 7.4 at 37° C. In a particular embodiment, the present invention contemplates a protein comprising an amino acid sequence of human Arginase I or II and a non-native metal cofactor, wherein said protein exhibits a $k_{cat}/K_M$ greater than 400 $mM^{-1}$ $s^{-1}$ at 37° C., pH 7.4.

Yet another aspect of the present disclosure is methods of treating cancer or tumors by arginine depletion in conjunction with an immunotherapeutic treatment targeting an immune checkpoint pathway, for example. arginine depletion can be accomplished with administration of a human Arginase I or Arginase II enzyme, including engineered or derivatized arginase enzymes as well as arginase or other arginine depleting enzymes from other species that exhibit at least an additive or synergistic effect when administered with an immune checkpoint targeted therapy.

The present disclosure can be described in certain embodiments, therefore, as a method of inhibiting tumor growth in a subject, comprising administering a pharmaceutical composition including a therapeutic amount of a human Arginase I enzyme comprising a cobalt cofactor and an immuno-oncology agent. The tumor can be of various types that respond to arginine depletion therapy and in certain embodiments is an arginine auxotrophic tumor, or includes arginine dependent or auxotrophic cells. In certain embodiments the auxotrophic cells exhibit a reduced or inhibited expression of one or more of ASS, OTC, ASL, or a combination thereof, thus requiring the tumor cell to utilize arginine from the serum.

In certain embodiments the human Arginase I or other enzyme is stabilized by association with a stabilizing agent in order to increase the half-life of the enzyme in the serum of a patient. As used herein "association" can include any of a number of types of association including, but not limited to covalent or non-covalent bonds, and can also include a protein fusion expressed from an engineered nucleic acid construct, from a hydrogen bonding or hydrophobic interaction and others known to those of skill in the art. Stabilizing agents for use in the disclosed methods can include but are not limited to polyethylene glycol, often referred to as pegylation, conjugation to one or more homogenous synthetic protein polymers, referred to as extenylation and commercially available under the trade name Xten®, conjugation to one or more Fc fragments or to a serum protein like albumin, for example. All such stabilized enzymes and others that would occur to those of skill in this art are contemplated by the present disclosure.

The disclosed methods are applicable to both human and non-human animal subjects including but not limited to veterinary, agricultural, domestic or research animals. It is an aspect of the disclosure that the immuno-oncology agent enhances the subject's immune response. In certain embodiments enhancing an immune system includes increasing activity of a patient's T-cell response to the presence of a tumor. In certain embodiments, therefore, the immuno-oncology agent inhibits an immune suppressor, which is sometimes a cell surface receptor referred to as a checkpoint inhibitor, or a ligand for such a receptor. Examples include, but are not limited to PD-1 pathway inhibitors such as an anti-PD-1 antibody or an anti-PD-L1 antibody, OX40 (CD134) pathway inhibitors such as anti-OX40 or anti-OX40L (CD252), anti-4-1BB or other anti B7 family ligands such as anti-B7-H1 and anti-B7.1 for example. Exemplary antibodies include but are not limited to pembrolizumab, ipilimumab, atezolizumab or nivolumab.

The methods of the disclosure are contemplated for the treatment of any responsive cancer or tumor, including, but not limited to hepatocellular carcinoma, renal cell carcinoma, breast cancer, melanoma, prostate cancer, pancreatic cancer, bladder cancer, colon carcinoma, colorectal cancer, triple negative breast cancer, Hodgkin's lymphoma, gastric cancer, glioblastoma, Merkel cell carcinoma, lung carcinoma, small cell lung cancers or non-small cell lung cancers. The administration of a combination of the human Arginase I enzyme and the anti-PD-1 antibody or anti-PDL-1 antibody or other immune checkpoint or TNF receptor inhibitors can exhibit an additive effect on tumor growth inhibition compared to the tumor growth inhibition exhibited by administering a therapeutic dose of the anti-PD-1 antibody alone or the anti-PD-Li antibody alone, or the human Arginase I enzyme alone, or in certain embodiments exhibits a greater than additive, or synergistic effect on the tumor growth or cancer. The two treatment regimens can be administered concurrently or they can be administered sequentially as needed.

The current disclosure can also be described in certain embodiments as a method of treating cancer in a cancer patient comprising administering to said patient a therapeutic amount of a pharmaceutical composition comprising a pegylated human Arginase I enzyme comprising a cobalt cofactor and an immune system modulating therapy comprising administering a pharmaceutical composition comprising an immuno-oncology agent.

In certain embodiments a therapeutic amount of the pegylated human Arginase I enzyme comprising a cobalt cofactor is from about 0.01 mg/kg to about 7.5 mg/kg, about 0.05 mg/kg to about 5 mg/kg, or about 0.1 mg/kg to about 5 mg/kg, or any amount derivable from or contained within the preceding ranges.

The pharmaceutical composition including a pegylated human Arginase I enzyme comprising a cobalt cofactor can be administered parenterally, or it can be delivered by various routes known in the art, including but not limited to topically, subcutaneously, intravenously, intradermally, intraarterially, intraperitoneally, intralesionally, intracranially, intraarticularly, intraprostatically, intrapleurally, intratracheally, intraocularly, intranasally, intravitreally, intravaginally, intrarectally, intramuscularly, subcutaneously, subconjunctivally, intravesicularlly, mucosally, intrapericardially, intraumbilically, orally, by inhalation, by injection, by infusion, by continuous infusion, by localized perfusion bathing target cells directly, via a catheter, or via a lavage. In certain embodiments the pharmaceutical composition is administered intravenously or subcutaneously.

The disclosure can also be described as a method of treating cancer in a cancer patient comprising administering to said patient an arginine depleting agent and a checkpoint pathway inhibitor or other immune system modulator that inhibits or reduces cancer growth or proliferation. The methods further include treatment of cancers in which the therapeutic effect of treatment with the arginine depleting agent and a checkpoint pathway inhibitor is additive as compared to treatment the arginine depleting agent alone or said checkpoint pathway inhibitor alone, or in which the therapeutic effect of treatment with said arginine depleting agent and a checkpoint pathway inhibitor is synergistic as compared to treatment the arginine depleting agent alone or said checkpoint pathway inhibitor alone. In certain embodiments the treatment can result in from 50% to 99%, or from 90% to 99% reduction in serum arginine in the patient, or reduction of serum arginine in a patient to an undetectable level.

Enzymes useful in the practice of the methods can include arginase enzymes, arginine deiminase enzymes or a combination thereof. The enzymes can be human enzymes, recombinant human enzymes, engineered human enzymes or enzymes from other species, either mammalian or bacterial, for example, including but not limited to *mycoplasma*.

In some embodiments, the native arginase is modified only by the substitution of the metal cofactor. In other embodiments, the arginase is modified by substitution of the metal cofactor in addition to other modifications, such as substitutions, deletions, truncations, or stabilization by conjugation to a stabilizing protein or polymer, such as by pegylation. In a particular embodiment, the invention provides a protein comprising a native amino acid sequence of human Arginase I or II and a non-native metal cofactor, wherein the amino acid sequence is lacking part of the native sequence. In particular embodiments, the non-native metal cofactor is cobalt. In some embodiments, the arginase lacks a portion of the wild-type sequence. In other embodiments, the amino acid sequence comprises a truncated Arginase I or Arginase II sequence. In a particular embodiment, the arginase is Arginase II and lacks the first 21 amino acids of the wild-type sequence. In another embodiment, the native arginases lacks an N-terminal methionine.

In another aspect, the present invention contemplates an arginase protein comprising at least one amino acid substitution, wherein the protein displays an increased catalytic activity under physiological conditions and especially at the pH of human serum (pH 7.4) when compared with native human Arginase I or II protein. In some embodiments, the arginase protein is a human Arginase I protein or human Arginase II protein. In some embodiments, the protein further comprises a non-native metal cofactor. In particular embodiments, the non-native metal cofactor is $Co^{+2}$. Substitution of the $Mn^{+2}$ cofactor with $Co^{+2}$ results in marked increase in catalytic activity and a drastic reduction in $K_M$ at physiological pH. In some aspects, the present invention also contemplates fusion proteins comprising an arginase linked to a non-arginase amino acid sequence. In one embodiment, the non-arginase sequence comprises at least a portion of the Fc region of an immunoglobulin, e.g., to increase the half-life of the arginase in serum when administered to a patient. The Fc region or portion thereof may be any suitable Fc region. In one embodiment, the Fc region or portion thereof is an IgG Fc region. In some embodiments, the amino acid sequence having arginase activity is selected from the group consisting of a native or mutated amino acid sequence of human Arginase I and a native or mutated amino acid sequence of human Arginase II or other arginine depleting enzymes known in the art. In certain embodiments, a dimeric Fc-arginase fusion protein, albumin, or a synthetic protein conjugation is contemplated.

The arginase in the fusion protein may be native, mutated, and/or otherwise modified, e.g., metal cofactor modified. In some embodiments, the arginase may contain deletions, substitutions, truncations or a combination thereof. In a particular embodiment, the present invention contemplates an Fc-arginase containing fusion protein, wherein the arginase is an Arginase I. In one embodiment, the arginase lacks a portion of the wild-type sequence. In another embodiment, the arginase is Arginase I lacking an N-terminal methionine. In yet another embodiment, the arginase is Arginase II, wherein the Arginase II lacks the first 21 amino acids of the wild-type Arginase II sequence. In some embodiments, the arginase further comprises a non-native metal cofactor. In these embodiments, either or both sites can be substituted to generate a fusion protein comprising an amino acid sequence of human Arginase I or II and a non-native metal cofactor. In some embodiments, the non-native metal cofactor is cobalt. In some embodiments, the arginase contains a substitution. Exemplary arginase enzymes for use in the present disclosure are more fully described in U.S. Pat. No. 8,440,184, incorporated herein in its entirety by reference.

The present invention also contemplates methods of treatment by the administration of the arginase proteins of the present invention, and in particular methods of treating subjects with cancer. In some embodiments, the cancer is one that does not express, or is otherwise deficient in, ASS, OTC, or ASL. In particular embodiments, the human cancer is an arginine auxotrophic cancer. As discussed above, the arginase protein may be native, mutated, and/or otherwise modified, e.g., metal cofactor modified. In one embodiment, the present invention contemplates a method of treating a human cancer patient comprising administering a formulation comprising a fusion protein, the fusion protein comprising an amino acid sequence having arginase activity and at least a portion of the Fc region of a human immunoglobulin to the patient. In some embodiments, the administration occurs under conditions such that at least a portion of the cancer cells of the cancer are killed. In another embodiment, the formulation comprises an amino acid sequence having human arginase activity higher than that displayed by the authentic human arginases at physiological conditions and further comprising one or more attached polyethylene glycol chain(s). In some embodiment, the formulation is a pharmaceutical formulation comprising any of the above discussed arginase proteins and a pharmaceutically acceptable excipients. Such pharmaceutically acceptable excipients are well known to those having skill in the art. All of the above arginase variants are contemplated as useful for human therapy.

The cancer may be any type of cancer or tumor type. In some embodiments, the cancer is hepatocellular carcinoma, renal cell carcinoma, melanoma, prostate cancer, or pancreatic cancer. In some embodiments, the formulation is administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

All of the above mentioned arginases, variants and the like are contemplated in a preferred embodiment as purified or isolated proteins, and preferably monomeric proteins.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the composition, device or method being employed to determine the value.

Following long-standing patent law, the words "a" and "an," when used in conjunction with the word "comprising" in the claims or specification, denotes one or more, unless specifically noted.

The term "therapeutically effective" as used herein refers to an amount of an active agent and/or therapeutic composition (such as a therapeutic polynucleotide and/or therapeutic polypeptide) that is employed in methods of the present invention to achieve a therapeutic effect, such as wherein at least one symptom of a condition being treated is at least ameliorated, and/or to the analysis of the processes or materials used in conjunction with these cells.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DESCRIPTION OF THE ILLUSTRATIVE EMBODIMENTS

Figure 1:
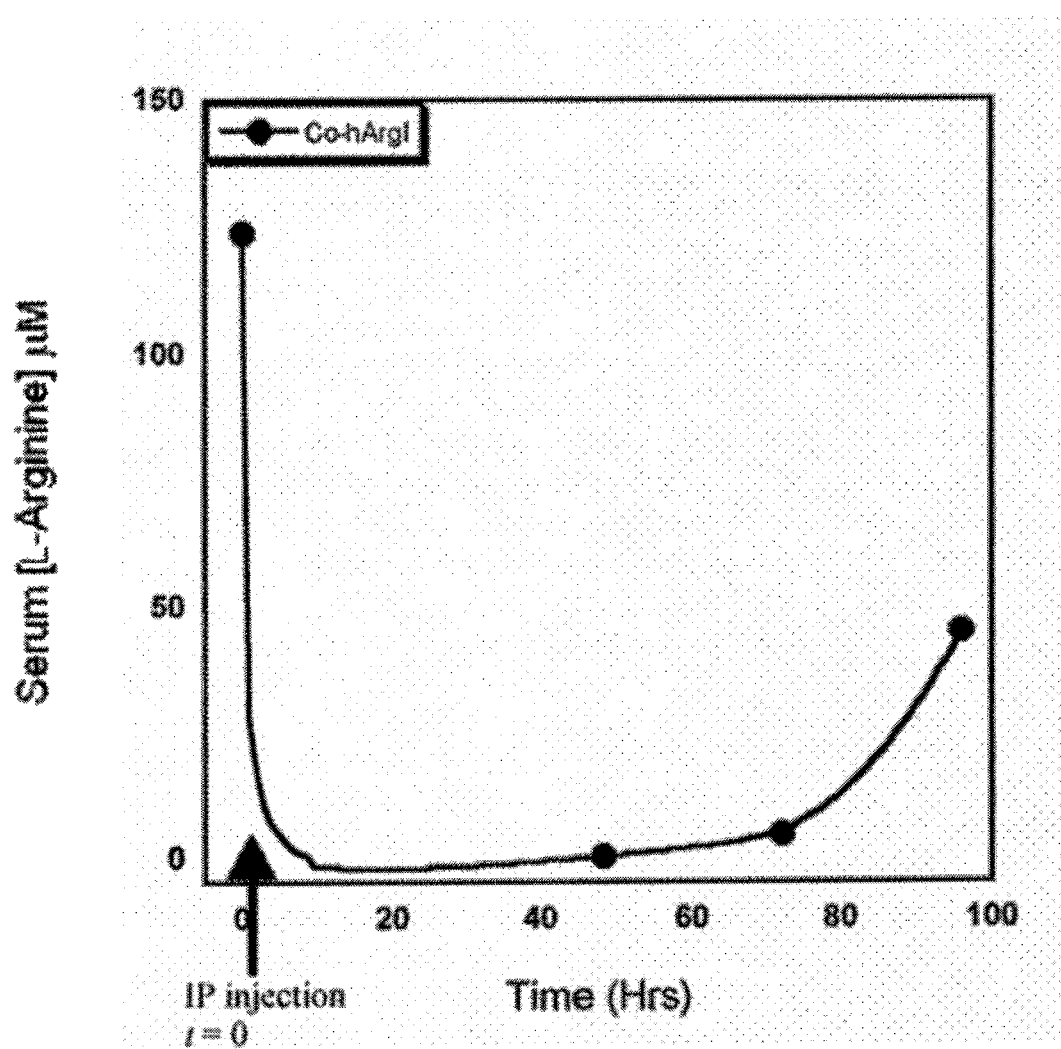
FIG. 1 is a graph showing serum L-arginine depletion in the mouse model. Serum L-Arg concentrations of Balb/c mice treated with a single IP dose of Co-hArgI are kept ≤ to 3-4 µM for over 3 days.

The invention generally relates to compositions and methods for the treatment of cancer with enzymes that deplete L-arginine in serum. In some embodiments, the cancer is one that does not express, or is otherwise deficient in, argininosuccinate synthetase (ASS), ornithine transcarbamylase (OTC), or argininosuccinate lyase (ASL), or other enzymes required for arginine biosynthesis. Both native and mutated enzymes are contemplated, as well as enzymes with modified metal cofactors, enzymes fused to other polypeptides as well as enzymes conjugated to polymers that increase serum persistence, e.g., high molecular weight polyethylene glycol

I. ARGINASE

Arginase is a manganese-containing enzyme. It is the final enzyme of the urea cycle. Arginase is the fifth and final step in the urea cycle, a series of biophysical reactions in mammals during which the body disposes of harmful ammonia. Specifically, arginases convert L-arginine into L-ornithine and urea.

L-arginine is the nitrogen donating substrate for nitric oxide synthase (NOS), producing L-citrulline and NO. Although the $K_M$ of arginase (2-5 mM) has been reported to be much higher than that of NOS for L-arginine (2-20 µM), arginase may also play a role in regulating NOS activity. Under certain conditions Arginase I is Cys-S-nitrosylated, resulting in higher affinity for L-arginine and reduced availability of substrate for NOS.

Arginase is a homo-trimeric enzyme with an α/β fold of a parallel eight-stranded βsheet surrounded by several helices. The enzyme contains a di-nuclear metal cluster that is integral to generating a hydroxide for nucleophilic attack on the guanidinium carbon of L-arginine. The native metal for arginase is $Mn^{2+}$. These $Mn^{2+}$ ions coordinate water, orientating and stabilizing the molecule and allowing water to act as a nucleophile and attack L-arginine, hydrolyzing it into ornithine and urea.

Mammals have two arginase isozymes (EC 3.5.3.1) that catalyze the hydrolysis of L-arginine to urea and L-ornithine. The Arginase I gene is located on chromosome 6 (6q.23), is highly expressed in the cytosol of hepatocytes, and functions in nitrogen removal as the final step of the urea cycle. The Arginase II gene is found on chromosome 14 (14q.24.1). Arginase II is mitochondrially located in tissues such as kidney, brain, and skeletal muscle where it is thought to provide a supply of L-ornithine for proline and polyamine biosynthesis (Lopez et al., 2005).

Arginases have been investigated for nearly 50 years as a method for degrading extracellular L-arginine (Dillon et al., 2002). Some promising clinical results have been achieved by introducing arginase by transhepatic arterial embolisation; following which, several patients experienced partial remission of HCC (Cheng et al., 2005). However, since arginase has a high $K_M$ (~2-5 mM) and exhibits very low activity at physiological pH values, high dosing is required for chemotherapeutic purposes (Dillon et al., 2002). While native arginase is cleared from circulation within minutes (Savoca et al., 1984), a single injection of PEG-arginase MW5000 in rats was sufficient to achieve near complete arginine depletion for ~3 days (Cheng et al., 2007).

Cheng et al. made the surprising observation that many human HCC cells lines do not express OTC (in addition to ASS) and thus they are susceptible to PEG-arginase (Cheng et al., 2007). In mice implanted with Hep3b hepatocarcinoma cells weekly administration of PEG-arginase resulted in tumor growth retardation which was accentuated by co-administration of 5-fluorouracil (5-FU). However, PEG-arginase was used at the very high doses that are impractical for human therapy, reflecting its lower physiological activity.

To address these issues a bacterial arginine hydrolyzing enzyme, arginine deiminase or ADI which displays good kinetics and stability has been tested in vitro and clinically. Unfortunately ADI is a bacterial enzyme and therefore it induces strong immune responses and adverse effects in most patients. However, for those patients who do not develop significant adverse responses, an impressive percentage exhibit stable disease or remission.

For clinical use, it is essential that the arginase is engineered to allow it to persist for long times (e.g., days) in circulation. In the absence of any modification, human arginase has a half-life of only a few minutes in circulation primarily because its size is not sufficiently large to avoid filtration though the kidneys. Unmodified human arginase is very susceptible to deactivation in serum and it is degraded with a half-life of only four hours. Therefore, the present invention developed novel and improved forms of arginase for clinical research and potential therapeutic use with improved circulation persistence.

II. ARGINASE VARIANTS

Mammals have two arginase isozymes (EC 3.5.3.1) that catalyze the hydrolysis of L-arginine to urea and L-ornithine. The Arginase I gene is located on chromosome 6 (6q.23), is highly expressed in the cytosol of hepatocytes, and functions in nitrogen removal as the final step of the urea cycle. The Arginase II gene is found on chromosome 14 (14q.24.1). Arginase II is mitochondrially located in tissues such as kidney, brain, and skeletal muscle where it is thought to provide a supply of L-ornithine for proline and polyamine biosynthesis (Lopez et al., 2005). L-arginine is the sole substrate for nitric oxide synthase (NOS), producing L-citrulline and NO. Although the $K_M$ of arginase (2-5 mM) has been reported to be much higher than that of NOS for L-arginine (2-20 µM), arginase may also play a role in regulating NOS activity (Durante et al., 2007). Under certain conditions Arginase I is Cys-S-nitrosylated, resulting in higher affinity for L-arginine and reduced availability of substrate for NOS (Santhanam et al., 2007). Arginase is a homo-trimeric enzyme with an α/β fold of a parallel eight-stranded n-sheet surrounded by several helices. The enzyme contains a di-nuclear metal cluster that is integral to generating a hydroxide for nucleophilic attack on the guanidinium carbon of L-arginine (Cama et al., 2003; Dowling et al., 2008). The native metal for arginase is $Mn^{2+}$. arginase with the native metal (i.e. Mn2+) exhibits a pH optimum of 9. At physiological pH the enzyme exhibits more than a 10-fold lower $k_{cat}/K_M$. in the hydrolysis of L-arginine. The low catalytic activity displayed by the authentic human arginase with the native $Mn^{2+}$ enzyme presents a problem for human therapy since it means that impractical doses of the enzyme may have to be used to achieve a therapeutically relevant reduction in L-arginine plasma levels.

In some aspects, the present invention contemplates mutant arginases wherein the natural metal cofactor ($Mn^{2+}$) is replaced with another metal. It has been found that substitution of the metal cofactor in human arginase exerts a beneficial effect on the rate of hydrolysis of L-Arginine and stability under physiological conditions when compared to native human arginase with the natural metal cofactor. The substitution of the native metal ($Mn^{2+}$) with other divalent cations can be exploited to shift the pH optimum of the enzyme to a lower values and thus achieve high rates of L-arginine hydrolysis under physiological conditions. Human Arginase I and II proteins of the present invention have two Mn (II) sites; therefore, either or both sites can be substituted so as to generate a mutated Arginase I or II protein with a non-native metal cofactor.

In some embodiments, the metal is cobalt ($Co^{2+}$). Incorporation of Co2+ in the place of $Mn^{2+}$ in human Arginase I or human Arginase II results in dramatically higher activity at physiological pH. It was found that a human Arginase I enzyme containing $Co^{2+}$ ("Co-hArgI") displayed a 10 fold increase in $k_{cat}/K_M$ in vitro at pH 7.4, which in turn translated into a 15 fold increase in HCC cytotoxicity and a 13-fold increase in melanoma cytotoxicity as compared to the human Arginase I which contains $Mn^{2+}$ ("Mn-hArgI"). It was also found that a pharmacological preparation of Co-hArgI could clear serum L-Arg for over 3 days in mice with a single injection. Furthermore, it was found that a pharmacological preparation of Co-hArgI could shrink HCC tumor xenografts in nude mice whereas Mn-hArgI only slowed tumor growth (Ensor et al., 2002).

In certain aspects of the invention, methods and compositions related to pegylated arginase are disclosed. Specifically, pegylation of arginase at an engineered cysteine residue (e.g., substituting the third residue of the N-terminal) may be used to produce a homogenous pegylated arginase composition. Methods for isolation of pegylated arginase based on temporary disruption of polymerization are also disclosed.

Pegylation is the process of covalent attachment of poly (ethylene glycol) polymer chains to another molecule, normally a drug or therapeutic protein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins.

The first step in pegylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation pegylation chemistry more efficient functional groups such as aldehyde, esters, amides etc. made available for conjugation.

As applications of pegylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific pegylation at native cysteinyl residues is seldom carried out, since these residues are usually in the form of disulfide bonds or are required for biological activity. On the other hand, site-directed mutagenesis can be used to incorporate cysteinyl pegylation sites for thiol-specific linkers. The cysteine mutation must be designed such that it is accessible to the pegylation reagent and is still biologically active after pegylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the pegylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However; this chemical is highly toxic and must be handled cautiously, particularly at lower pH where it becomes volatile.

Due to the multiple lysine residues on most proteins, site-specific pegylation can be a challenge. Fortunately, because these reagents react with unprotonated amino groups, it is possible to direct the pegylation to lower-pK amino groups by performing the reaction at a lower pH. Generally the pK of the α-amino group is 1-2 pH units lower than the epsilon-amino group of lysine residues. By PEGylating the molecule at pH 7 or below, high selectivity for the N-terminus frequently can be attained. However; this is only feasible if the N-terminal portion of the protein is not required for biological activity. Still, the pharmacokinetic benefits from pegylation frequently outweigh a significant loss of in vitro bioactivity, resulting in a product with much greater in vivo bioactivity regardless of pegylation chemistry.

There are several parameters to consider when developing a pegylation procedure. Fortunately, there are usually no more than four or five key parameters. The "design of experiments" approach to optimization of pegylation conditions can be very useful. For thiol-specific pegylation reactions, parameters to consider include: protein concentration, PEG-to-protein ratio (on a molar basis), temperature, pH, reaction time, and in some instances, the exclusion of oxygen. Oxygen can contribute to intermolecular disulfide formation by the protein, which will reduce the yield of the PEGylated product. The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the pegylation reaction. For example, if the pegylation agent is only 70% active, the amount of PEG used should ensure that only active PEG molecules are counted in the protein-to-PEG reaction stoichiometry. How to determine PEG reactivity and quality will be described later.

IV. PROTEINS AND PEPTIDES

In certain embodiments, the present invention concerns novel compositions comprising at least one protein or peptide, such as stabilized arginase multimers. These peptides may be comprised in a fusion protein or conjugated to an agent as described supra.

A. Proteins and Peptides

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties. Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

| Modified and Unusual Amino Acids | |
|---|---|
| Abbr. | Amino Acid |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Alle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding, to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

B. Nucleic Acids and Vectors

In certain aspects of the invention, nucleic acid sequences encoding a fusion protein as a stabilized multimeric arginase may be disclosed. Depending on which expression system to be used, nucleic acid sequences can be selected based on conventional methods. For example, human arginase I and II contain multiple codons that are rarely utilized in *E. coli* that may interfere with expression, therefore the respective genes or variants thereof may be codon optimized for *E. coli* expression. Various vectors may be also used to express the protein of interest, such as a fusion multimeric arginase or a cysteine-substituted arginase. Exemplary vectors include, but are not limited, plasmid vectors, viral vectors, transposon or liposome-based vectors.

C. Host Cells

Host cells, preferably eukaryotic cells, useful in the present invention are any that may be transformed to allow the expression and secretion of arginase and fusion multimers thereof. The host cells may be bacteria, mammalian cells, yeast, or filamentous fungi. Various bacteria include *Escherichia* and *Bacillus*. Yeasts belonging to the genera *Saccharomyces, Kluyveromyces, Hansenula,* or *Pichia* would find use as an appropriate host cell. Various species of filamentous fungi may be used as expression hosts including the following genera: *Aspergillus, Trichoderma, Neurospora, Penicillium, Cephalosporium, Achlya, Podospora, Endothia, Mucor, Cochliobolus* and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) and *Schizosaccharomyces pombe*; filamentous fungi, e.g., *Aspergillus nidulans, Aspergillus awamori* (Ward, 1989), *Trichoderma reesei* (Penttila et al., 1987; Harkki et al, 1989).

Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCCCRL 1548) SV40-transformed monkey kidney cells (COS-1; ATCC CRL 1650) and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the arginase and/or their fusion multimers are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of the proteins are achieved.

D. Protein Purification

Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide always be provided in their most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, a stabilized arginase multimeric fusion protein, or an arginase prior or post pegylation. For example, a His tag or an affinity epitope may be comprised in such a arginase variant to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes such as proteins and industrial polymers. Typically, when an aqueous solution is used to transport the sample through the column, the technique is known as gel filtration chromatography, versus the name gel permeation chromatography which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or High pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

V. PHARMACEUTICAL COMPOSITIONS

It is contemplated that the novel arginases of the present invention can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g. cancer that the surgery failed to eliminate) does not survive.

It is not intended that the present invention be limited by the particular nature of the therapeutic preparation. For example, such compositions can be provided in formulations together with physiologically tolerable liquid, gel or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Where clinical applications are contemplated, it may be necessary to prepare pharmaceutical compositions—expression vectors, virus stocks, proteins, antibodies and drugs—in a form appropriate for the intended application. Generally, pharmaceutical compositions of the present invention comprise an effective amount of one or more arginase variants or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one arginase variant, such as a stabilized multimeric arginase or a pegylated arginase isolated by the method disclosed herein, or additional active ingredient will be known to those of skill in the art in light of the present disclosure, as exemplified by Remington's Pharmaceutical Sciences, $18^{th}$ Ed., 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, $18^{th}$ Ed., 1990, incorporated herein by reference). Except insofar as any conventional carrier is incompatible with the active ingredient, its use in the pharmaceutical compositions is contemplated.

The present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18$^{th}$ Ed., 1990, incorporated herein by reference).

The arginase variants may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include arginase variants, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the stabilized multimeric or pegylated arginase may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

VII. DEFINITIONS

The term "aa" refers to amino acid(s). Amino acid substitutions are indicated by the amino acid position, e.g. 303, in the molecule using a letter code (the letter in front of the number indicates the amino acid being replaced, while the letter after the number indicates the amino acid being introduced).

As used herein the term "portion" when in reference to a protein (as in "a portion of a given protein") refers to fragments of that protein. The fragments may range in size from four amino acid residues to the entire amino acid sequence minus one amino acid.

As used herein the terms "protein" and "polypeptide" refer to compounds comprising amino acids joined via peptide bonds and are used interchangeably.

As used herein, the term "fusion protein" refers to a chimeric protein containing the protein of interest (i.e., a human arginase or variant thereof) joined (or operably linked) to an exogenous protein fragment (the fusion partner which consists of a non-arginase protein). The fusion partner may enhance serum half-life, solubility, or both. It may also provide an affinity tag (e.g. his-tag) to allow purification of the recombinant fusion protein from the host cell or culture supernatant, or both.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term $k_{cat}$ as used herein refers to the turnover number or the number of substrate molecule each enzyme site converts to product per unit time, and in which the enzyme is working at maximum efficiency.

The term $K_{cat}/K_m$ as used herein is the specificity constant which is a measure of how efficiently an enzyme converts a substrate into product.

The term "Mn-hArgI" refers to human Arginase I with an Mn (II) cofactor. The term "Co-hArgI" refers to human Arginase I (mutant or native) with a Co (II) cofactor. The term "$IC_{50}$" is the half maximal (50%) inhibitory concentration (IC) and thus a measure of effectiveness.

The term "pegylated" refers to conjugation with polyethylene glycol (PEG), which has been widely used as a drug carrier, given its high degree of biocompatibility and ease of modification. (Harris et al., 2001). Attachment to various drugs, proteins, and liposomes has been shown to improve residence time and decrease toxicity. (Greenwald et al., 2000; Zalipsky et al., 1997). PEG can be coupled (e.g. covalently linked) to active agents through the hydroxyl groups at the ends of the chain and via other chemical methods; however, PEG itself is limited to at most two active agents per molecule. In a different approach, copolymers of PEG and amino acids have been explored as novel biomaterials which would retain the biocompatibility properties of PEG, but which would have the added advantage of numerous attachment points per molecule (providing greater drug loading), and which can be synthetically designed to suit a variety of applications (Nathan et al., 1992; Nathan et al., 1993).

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "subject" refers to animals, including humans.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "variant" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

VIII. KITS

The present invention provides kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a stabilized multimeric arginase or isolated pegylated arginase, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

IX. EXAMPLES

The following examples serve to illustrate certain preferred embodiments and aspects of the present invention and are not to be construed as limiting the scope thereof. In the experimental disclosure which follows, the following abbreviations apply: eq (equivalents); M (Molar); µM (micromolar); mM (millimolar); N (Normal); mol (moles); mmol (millimoles); µmol (micromoles); nmol (nanomoles); g (grams); mg (milligrams); µg (micrograms); L (liters); ml (milliliters); µl (microliters); cm (centimeters); mm (millimeters); µm (micrometers); nm (nanometers); EC (degrees Centigrade); MW (molecular weight); PBS (phosphate buffered saline); min (minutes).

Example 1

Incorporating and Determining Metal Content in Arginase I

Incorporation of $Mn^{2+}$ and $Co^{2+}$ can be achieved by purifying arginase, followed by an incubation step with 10 mM metal at 50° C. for 10 minutes. In order to determine the final metal content and identity of the arginase preparations, protein samples of Mn-hArgI (145 µM), Co-hArgI (182 µM) and associated dialysis buffers (100 mM Hepes, pH 7.4) were diluted in 2% nitric acid and analyzed by inductively coupled plasma mass spectrometry (ICP-MS, Department of Geological Sciences, University of Texas at Austin) to quantify the protein's cobalt, iron, manganese and zinc content by subtracting the concentration of metals found in the dialysis buffer from the metal concentration of the final protein samples and dividing by protein concentration. To determine protein concentrations, an extinction coefficient was calculated for hArgI based on the amino acid sequence (Gill and von Hippel, 1989). All protein concentrations for Arginase I were calculated based upon the calculated $\epsilon_{280}=24{,}180$ $M^{-1}$ $cm^{-1}$ in a final buffer concentration of 6 M guanidinium hydrochloride, 20 mM phosphate buffer, pH 6.5. For comparison, arginase concentration was also calculated by BCA assay using dilutions of BSA as a standard. Using this method it was found that arginase samples incubated with $Co^{2+}$ contain 2.1±0.5 equivalents Co and 0.4±0.1 equivalents Fe, with no detectable amounts of Zn or Mn. Samples incubated with $Mn^{2+}$ contain 1.5±0.2 equivalents Mn and 0.4±0.1 equivalents Fe, and no detectable amounts of Zn or Co. Thus, heat incubation is an efficient method for incorporation of cobalt.

Additional studies of cobalt loading have demonstrated that a higher proportion of cobalt loading is achievable and results in a higher specific activity. The results of these studies is shown on the following table and in FIG. 3.

TABLE 2

| Co-Arginase I Cobalt Loading | | | | | |
|---|---|---|---|---|---|
| Identity | Co (mM) | Temp (° C.) | Time (Min) | Total Co (µg/mg Arginase) | Total Mn (µg/mg Arginase) | Specific Activity (U/mg) |
| APO-Arginase I* | NA | NA | NA | <0.025 | 0.008 | 24 |
| APO Loading 1* | 0.1 | 5 | 15 | 0.3 | ND | 117 |
| Coh-Arg I* | 10 | 20 | 60 | 2 | 0.06 | 410 |
| APO Loading 2* | 1 | 5 | 15 | 2.4 | ND | 395 |
| APO Loading 3* | 10 | 20 | 15 | 2.8 | ND | 493 |
| APO Loading 4* | 10 | 20 | 60 | 2.9 | ND | 489 |
| APO Loading 5 | 10 | 37 | 15 | 2.8 | ND | NT |
| APO Loading 6 | 10 | 53 | 15 | 2.6 | ND | NT |
| Co-ArgI-PEG | 10 | 53 | 15 | 3 | ND | 500 |
| Theoretical | | | | 3.4 | | |

*Graphed

Figure 3:
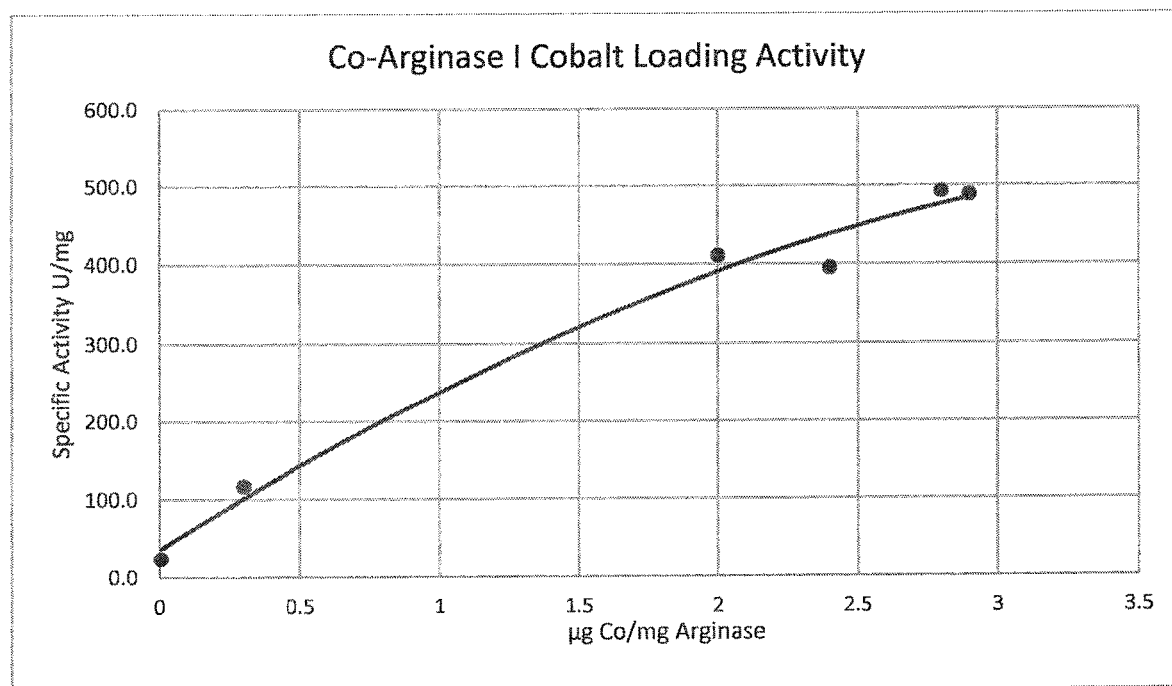
FIG. 3 is a graph showing the effect of cobalt loading on the catalytic activity of human Arginase I.

The starred data are shown in FIG. 3.

Example 2

Cytotoxicity of Co-Arg and its Variants Towards Hepatocellular Carcinoma Cells and Metastatic Melanomas In order to test the in vitro cytotoxicity of engineered arginase, varying concentrations (0-100 nM) of Mn-ArgI, Co-ArgI, or Co-hArgI variants were incubated with HCC (Hep 3b) cells or melanoma (A375) cells (American Type Culture Collection) in 96-well plates at a seeding density of 500 cells/well, in DMEM media supplemented with fetal bovine serum. After 24 hours of incubation at 37° C., the cells were treated with arginase containing media in triplicate at various concentrations. The control solution was a balanced salt solution in media. The treated cells were maintained at 37° C. and 5% $CO_2$. Cells were tested by standard MTT assay (Sigma-Aldrich) on days 1, 3, 5, & 7 by addition of 100 µL/well of MTT (5 mg/mL), and incubated for 4 hours with gentle agitation one to two times per hour. Following this, the solution was aspirated and 200 µL of DMSO was then added to each well. Absorbance at 570 nm was interpreted for each well using an automated plate reader to determine the relative number of surviving cells compared to controls. The resulting data was fit to an exponential equation to determine an apparent $IC_{50}$ value for arginase cytotoxicity. The $IC_{50}$ values from day 5 were calculated, yielding an $IC_{50}$ value for Mn-hArgI of 5±0.3 nM (~0.18 µg/ml) and a value of 0.33±0.02 nM for Co-hArgI (~0.012 µg/ml). Thus, the Co-ArgI enzyme appears to be 15 fold more cytotoxic than the Mn substituted enzyme against HCC. Against the metastatic melanoma cell line (A375) Mn-hArgI resulted in an apparent $IC_{50}$ of 4.1±0.1 nM (~0.15 µg/ml). Incubation with Co-hArgI lead to a 13-fold increase in cytotoxicity with an apparent $IC_{50}$ of 0.32±0.06 nM (~0.012 µg/ml).

Example 3

Engineering an Fc-Arginase Fusion Protein for Enhanced In Vivo Half-Life

Fusion to the IgG Fc domain has been employed extensively for prolonging the in vivo half-lives of therapeutic polypeptides such as the TNF-α inhibitor etanercept (Enbril™). The Fc domain binds to the FcγRn receptor, which is expressed on vascular endothelium and many other tissues (Roopenian and Akilesh, 2007). The affinity of FcγRn for the IgG Fc domain is strongly pH dependent. Binding occurs at the acidic pH of endosomal compartments allowing the protein to be recycled onto the cell surface and thus escape proteolytic degradation. At the cell surface, the Fc domain is released from FcγRn because the binding affinity is very low at physiological pH. Endosomal recycling via FcγRn is estimated to increase the serum half-life of immunoglobulins at least 4-7 fold, to about 7-14 days in humans. Fc fusions exploit this property to endow short lived molecules with a long half-life. However, the human arginase is a homotrimer and therefore if fused to the IgG Fc, which itself is a dimer, the resulting Fc-arginase polypeptide will likely form high molecular weight aggregates.

This problem was avoided by employing mutant forms of arginase that disrupt trimerization and are stable in the monomeric form. The trimerization and subunit interface of Arginase I have been studied in some detail (Lavulo et al., 2001). A single amino acid substitution at Glu256Gln has been shown to disrupt trimerization resulting in the formation of monomeric Arginase I enzyme (Sabio et al., 2001). After expression and purification of this variant, the steady-state kinetic analysis revealed nearly identical activity compared to Co-hArgI with a $k_{cat}/K_M$ of 1,320 s$^{-1}$ mM$^{-1}$.

This construct was then cloned into Fc expression vectors. The Fc expression vector is a construct based on a pTRC99a plasmid (Amersham) that contains a DsbA leader sequence followed by the IgG Fc coding region, an EcoRI restriction site and a stop codon. The monomeric arginase gene was placed in frame behind the Fc coding region by digesting both vector and gene with EcoRI, and was subsequently ligated and transformed into *E. coli* (BL21) for sequencing and expression. Since the IgG Fc is normally a glycosylated protein, expression of recombinant IgGs or of Fc fusions has so far been carried out in recombinant mammalian cells that, unlike bacteria, are capable of N-linked glycosylation. However, while glycosylation at Asn297 is critical for the binding to the activating and inhibitory Fcγ receptors (FcγRI-III in humans) it does not have a noticeable effect on the affinity or pH dependent binding to FcγRn (Tao and Morrison, 1989; Simmons et al., 2002). Thus, aglycosylated IgG antibodies expressed in bacteria exhibit serum persistence in primates nearly indistinguishable from that of fully glycosylated antibodies expressed in mammalian cells (Simmons et al., 2002). In contrast to prevailing earlier notions, IgG antibodies and Fc proteins can be expressed efficiently in *E. coli* up to g/L levels in fermenters. *E. coli* expression is technically much simpler and faster. In addition, since the resulting protein is aglycosylated, it does not display glycan heterogeneity, an important issue in the expression of therapeutic glycoproteins (Jefferis, 2007). The fusion protein is purified by Protein A chromatography and the yield of correctly folded, dimeric Fc-arginase fusion relative to polypeptides that fail to dimerize is quantified by FPLC gel filtration chromatography. This formulation has led to a highly active and very stable form of human arginase, suitable for in vivo trials.

Example 4

Pegylation of Arginase

Arginase was purified and was then made 10 mM with CoCl$_2$ and heated at 50° C. for 10 minutes. After centrifuging to remove any precipitates, the PEG-5000 arginase was extensively buffer exchanged (PBS with 10% glycerol) using a 100,000 MWCO filtration device (Amicon), and sterilized with a 0.2 micron syringe filter (VWR). All pegylated enzyme was analyzed for lipopolysaccharide (LPS) content using a Limulus Amebocyte Lysate (LAL) kit (Cape Cod Incorporated).

Pegylated Co-hArgI was found to have nearly identical serum stability to wild type enzyme and displayed a $k_{cat}/K_M$ value of 1690±290 s$^{-1}$ mM$^{-1}$.

Example 5

Serum Depletion of L-Arg in the Mouse Model

Balb/c mice were treated by single IP injection with 500 µg of pharmacologically prepared, pegylated Co-hArgI or an equal volume of PBS. Mice were sacrificed by cardiac veni-puncture for blood collection at the time points of 0, 48, 72, and 96 hrs. Blood samples were immediately mixed 50:50 (v/v) with a 400 mM sodium citrate buffer pH 4, allowed to clot for 30 minutes and centrifuged for serum separation. The resulting serum was then filtered on a 10,000 MWCO device (Amicon) for the removal of large proteins and precipitates and the flow-through was collected for analysis. L-arginine standards, control mouse serum and experimental samples were derivatized with OPA (Agilent) and separated on a C18 reverse phase HPLC column (Agilent) (5 µm, 4.6×150 mm) essentially as described by Agilent Technologies (Publication Number: 5980-3088) except for modification of the separation protocol slightly by reducing the flow rate by ½ and doubling the acquisition time to get better peak separation. An L-arginine standard curve was constructed by plotting L-Arg peak area versus concentration in order to quantify serum L-Arg levels. A single dose of pharmacologically prepared Co-hArgI was sufficient to keep L-Arg at or below detection limits for over 3 days (FIG. 1).

Example 6

HCC Tumor Xenograft Treatment with Co-hArgI

Figure 2:
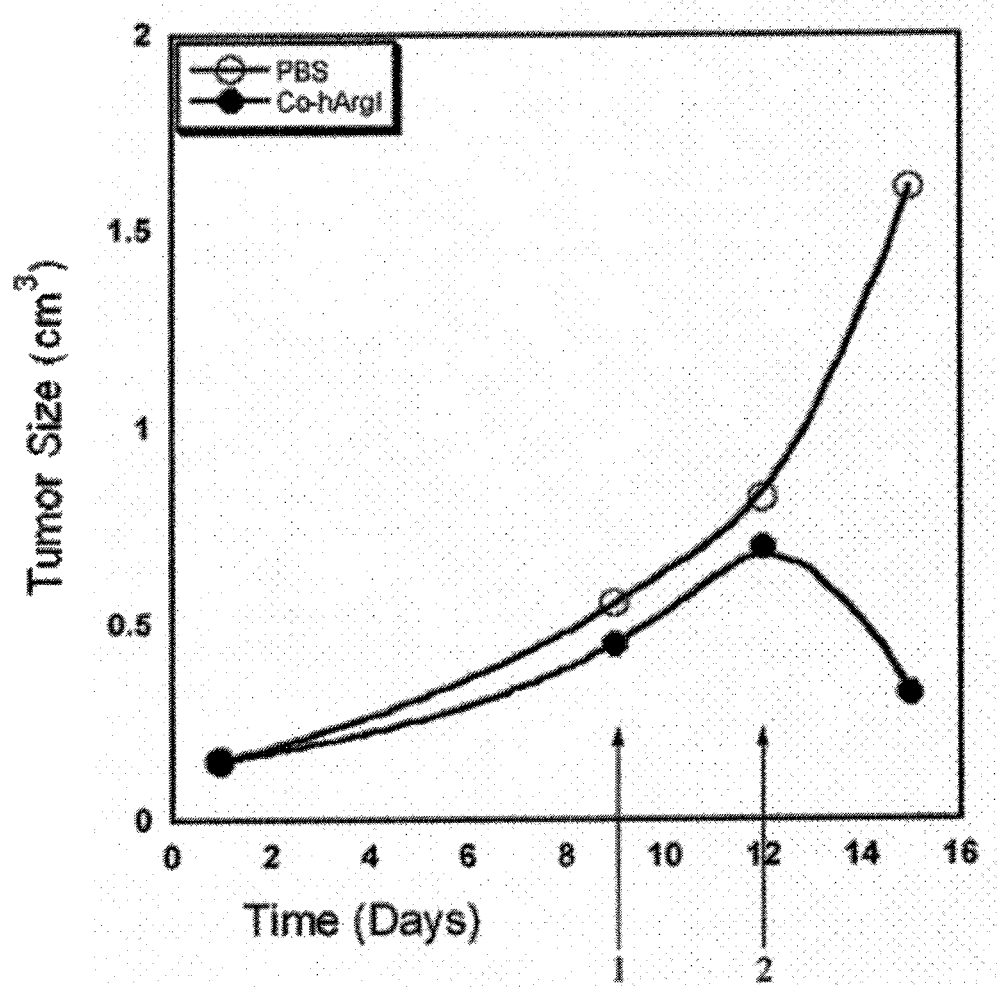
FIG. 2 is a graph showing HCC tumor xenograft reduction when treated with Co-hArgI as compared to controls. Nude mice bearing a Hep3b tumor xenografts were treated twice by IP injection with either PBS (°) or Co-hArgI (●) at day 9 and at day 12. Tumor shrinkage was observed in the mice treated with Co-hArgI whereas PBS treated tumors grew unchecked.

Nude mice were injected subcutaneously in the flank with ~10$^6$ HCC cells collected from a 75% confluent tissue culture. After the HCC xenografted tumors had grown to ~0.5 cm$^3$ in diameter (Day 9), mice were sorted into two groups. The experimental group received a 500 µg IP injection of pharmacologically optimized Co-hArgI at day 9 and at day 12. The control group received IP injections of PBS at days 9 and 12. As can be seen in FIG. 2, the PBS treated tumors had increased 3-fold in size by day 15. In stark contrast, Co-hArgI treated tumors had decreased in size by day 15. Mn-hArgI treated tumors had only been shown to be retarded in growth rate (Cheng et al., 2007). Co-hArgI appears to be a highly effective chemotherapeutic agent against HCCs both in vitro and in vivo.

Example 7

Disruption of the L-Arginine Balance in the Tumor Microenvironment with Co-hArgI and Anti-PD-L1 Ab Human arginase I (hArgI) is a Mn$^{2+}$-dependent enzyme that displays low activity and low stability in serum. Myeloid-derived suppressor cells (MDSC) express hArgI and nitric-oxide synthase (NOS), which control the availability of L-arginine in the tumor microenvironment and in turn regulate the function of T-cells. Depletion of L-arginine by MDSC has been correlated to impairment of T-cell anti-tumor function and tumor evasion of host immunity. The expression of enzymes of the L-arginine biosynthetic pathway in peripheral blood mononuclear cells, bone marrow mononuclear cells and CD34$^+$ cells was analyzed revealing that these cells express low levels of OTC and ASS, suggestive of dependence of these cells on exogenous/extracellular L-arginine for physiological function. Based on this finding it is contemplated that long term depletion of L-arginine may negatively impact the MDSC population and therefore enhance immune regulation of tumor growth. This hypothesis was tested using engineered hArgI (AEB1102), developed by replacement of the Mn$^{2+}$ natural cofactor with Co$^{2+}$ which results in significantly improved catalytic activity and serum stability compared to endogenous hArgI. The engineered enzyme is also pegylated as described above. The effects of chronic, extensive pegylated Co-hArgI-mediated depletion of L-arginine in vivo in the murine CT26 colon-cancer model dosed alone and in combination with anti-PD-L1 and anti-PD-1 monoclonal antibodies (mAbs) were tested.

Female Envigo Balb/c mice (BALB/cAnNHsd) were used in these studies. They were 6-7 weeks old on Day 1 of the test. Test animals were implanted subcutaneously on Day 0 with 5.0E+05 CT26.WT cells. All mice were sorted into study groups and treatment was started as follows:

AEB-001-1037
Group 1: Vehicle (PBS) IP, Q7D×4; plus Isotype Control, 10 mg/kg IP, (Q3D×2; 3off)×4
Group 2: AEB1102, (3 mg/kg IP, Q7D×4)
Group 3: anti-PD-L1 Ab, 10 mg/kg IP, (Q3D×2; 3off)×4
Group 4: AEB1102, 3 mg/kg IP, Q7D×4; plus anti-PD-L1 Ab, 10 mg/kg IP, (Q3D×2; 3off)×4;
AEB1102 was dosed 4 times, once weekly, (Days 3, 10, 17, 24)
Anti-PD-L1 was dosed 8 times, one on two off, one on three off each week (Days 3, 6, 10, 13, 17, 20, 24, 27)

All animals were observed for clinical signs at least once daily. Individual body weights and tumor volumes were recorded three times weekly. Individual mice were terminated when tumor size reached a value of 2000 mm$^3$.

In vivo treatment of CT26 mice with AEB1102 (pegylated Co-hArgI) resulted in a therapeutic effect comparable to standard immunomodulatory antibodies that target PD-1 and PD-L1. Of significance, combination therapy of AEB1102 with anti-PD-1 and PD-L1 mAbs resulted in an apparently synergistic or at least additive anti-tumor effect compared to AEB1102 alone and immunotherapy alone.

Figure 4:
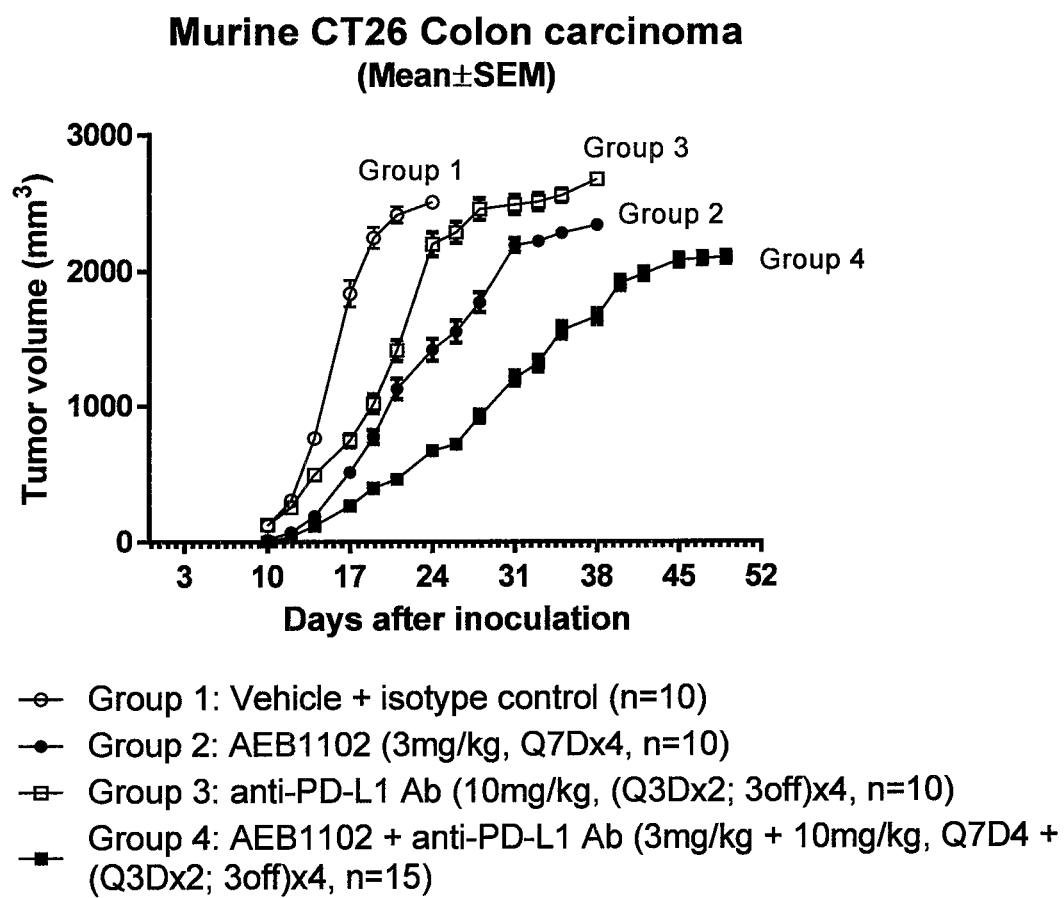
FIG. 4 is a graph showing colon carcinoma tumor growth inhibition in CT26 mouse model with Co-hArgI, anti PD-L1 and the combination of Co-hArgI and anti PD-L1. As seen in the data, the combination of the 2 agents has a greater than additive effect on inhibition of tumor growth.

The data from this study is shown graphically in FIG. 4. The data reflect the effect of treatment with a pegylated Co-hArgI in combination with an anti-immune checkpoint protein receptor (anti-PD-1) and ligand, (anti-PD-L1). In the figure the upper curve is an isotype control antibody, the second curve is anti-PD-L1 antibody, the third curve is pegylated Co-hArgI and the lowest curve is the combination treatment of the pegylated Co-hArgI and anti-PD-L1 antibody. As seen in the data, the combination of the 2 agents has a greater than additive effect on inhibition of tumor growth.

Figure 6:
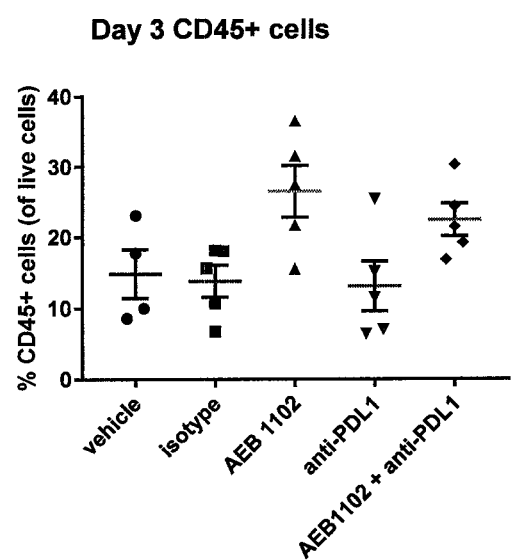
FIG. 6 is a graph showing CD45+ Tcells present in CT26 mouse model with Co-hArgI, anti PD-L1 and the combination of Co-hArgI and anti PD-L1.
Figure 7:
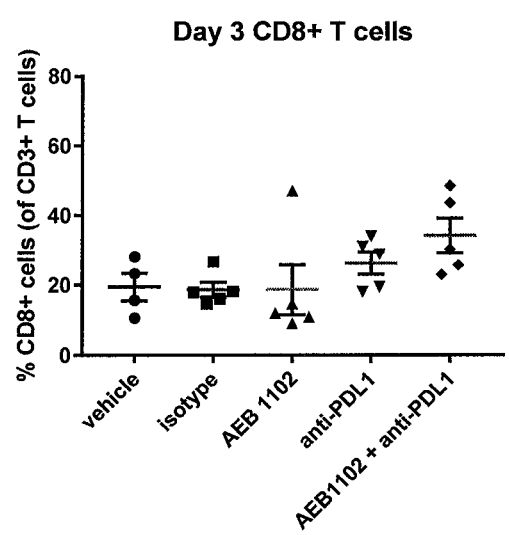
FIG. 7 is a graph showing percent CD8+ cells present in CD45+ Tcells as shown in FIG. 6.

The effect on lymphocyte Tcell activation was also measured in samples taken on day 3. The percentage of total live cells that expressed CD45+ in the four groups as well as the percentage of CD45+ cells that were also CD8+ are shown in Table 3. These data are also shown in graphical form in FIGS. 6 and 7.

| Groups | Day 3 CD45+ cells | Day 3 CD8+ cells |
| --- | --- | --- |
| Vehicle | 14.8 ± 3.4 | 19.4 ± 3.9 |
| Isotype | 13.8 ± 2.2 | 18.7 ± 2.1 |
| AEB1102 | 26.5 ± 3.7 | 18.7 ± 7.1 |
| anti-PD-L1 | 13.1 ± 3.5 | 26.3 ± 3.24 |
| AEB1102 + anti-PD-L1 | 22.4 ± 2.3 | 34.2 ± 5.0 |

Table reports mean ± SEM

Collectively these results demonstrate that disrupting the L-arginine physiological balance in the tumor microenvironment inhibits tumor growth and further sensitizes the tumor to immunotherapy.

Example 8

Effect of Treatment of Colon Carcinoma Treatment with ArgI and OX40

Suspensions of MC38 colon carcinoma cells were injected into the flanks of female C57BL/6 mice. When tumor volume reached 75-100 mm$^3$ on day 0, mice were randomized into groups. Tumor volume was measured twice a week using calipers. Treatments were started on Day 0.

Figure 5:
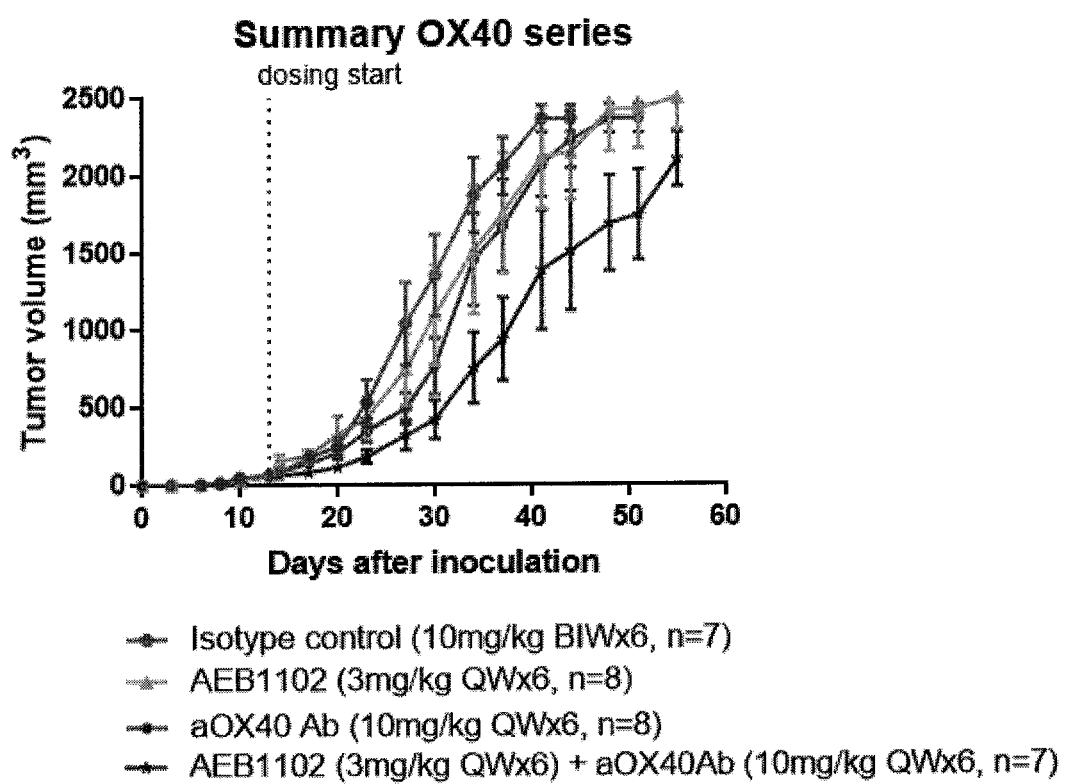
FIG. 5 is a graph showing colon carcinoma tumor growth inhibition in an MC38 mouse model with Co-hArgI, anti OX40 antibodies, and the combination of Co-hArgI and anti OX40 antibodies. As seen in the data, the combination of the 2 agents has a greater than additive effect on inhibition of tumor growth.

A first group was injected with 10 mg/kg isotype control biweekly for 6 weeks, second group was injected with 3 mg/kg co-Arginase I, weekly for 6 weeks, a third group was injected with 10 mg/kg anti-OX40ab weekly for 6 weeks, and a fourth group was injected with 3 mg/kg co-ArgI and 10 mg/kg anti OX40ab weekly for 6 weeks. The data from this study is shown in FIG. 5. Although it appears that the co-ArgI was given at a suboptimal dose, a trend is seen in which the combination of ArgI and aOX40 has a more than additive effect on the reduction or inhibition of tumor volume.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cama et al., Biochemistry, 42:7748-7758, 2003.
Cheng et al., Cancer Lett., 224:67-80, 2005.
Cheng et al., Cancer Res., 67:309, 2007.
Cheng et al., Cancer Res., 67:4869-4877, 2007.
Dillon et al., Med. Sci. Monit., 8:BR248-253, 2002.
Dowling et al., Cell Mol. Life. Sci., 65(13):2039-55, 2008.
Durante et al., Clin. Exp. Pharmacol. Physiol., 34:906-911, 2007.
Ensor et al., Cancer Res., 62:5443-5450, 2002.
Feun et al., J. Neurooncol., 82:177-181, 2007.
Gill and von Hippel, Anal. Biochem., 182:319-326, 1989.
Greenwald et al., Crit. Rev Therap Drug Carrier Syst., 17:101-161, 2000.
Harkki et al., BioTechnology, 7:596-603, 1989.
Harris et al., Clin. Pharmacokinet., 40(7):539-51, 2001.
Hopwood et al., In: Genetic Manipulation of *Streptomyces*, A Laboratory Manual, The John limes Foundation, Norwich, Conn., 1985.
Izzo et al., J. Clin. Oncol., 22:1815-1822, 2004.
Jefferis, Expert Opin. Biol. Ther., 7:1401-1413, 2007.
Lavulo et al., J. Biol. Chem., 276:14242-14248, 2001.
Lopez et al., Febs J., 272:4540-4548, 2005.
Lordanescu, J. Bacteriol, 12:597 601, 1975.
Mellor et al., Gene, 24:1-14, 1983.

Nathan et al., Bioconj Chem., 4:54-62, 1993.
Nathan et al., Macromolecules, 25:4476-4484, 1992.
Pardon, Drew, Nature Reviews Cancer 12, 252-264 (April 2012
Penttila et al., Gene, 61:155-164, 1987.
Remington's Pharmaceutical Sciences, 18th Ed. Mack Printing Company, 1289-1329, 1990.
Roopenian and Akilesh, Nat. Rev. Immunol., 7:715-725, 2007.
Sabio et al., FEBS Lett., 501:161-165, 2001.
Santhanam et al., Circ. Res., 101:692-702, 2007.
Savoca et al., Cancer Biochem. Biophys., 7:261-268, 1984.
Scott et al., Br. J. Cancer, 83:800-810, 2000.
Shen et al., Cancer Lett., 231:30-35, 2006.
Sibakov et al., Eur. J. Biochem., 145:567 572, 1984.
Simmons et al., J. Immunol. Methods, 263:133-147, 2002.
Tao et al., J. Immunol., 143:2595-2601, 1989.
Ward, Embo-Alko Workshop on Molecular Biology of Filamentous Fungi, Helsinki, 119-128, 1989.
Wheatley and Campbell, Pathol. Oncol. Res., 8:18-25, 2002.
Yoon et al., Int. J. Cancer, 120:897-905, 2007.
Zalipsky et al., Bioconjug Chem., 8:111-118, 1997.

The invention claimed is:

1. A method of inhibiting tumor growth in a subject, comprising administering to said subject a pharmaceutical composition comprising a therapeutically effective amount of a human Arginase I enzyme comprising a cobalt cofactor and a therapeutically effective amount of an immuno-oncology agent, wherein the immuno-oncology agent is selected from the group consisting of: pembrolizumab, ipilimumab, atezolizumab and nivolumab.

2. The method of claim 1, wherein the subject has a tumor that comprises arginine auxotrophic tumor cells.

3. The method of claim 1, wherein the human Arginase I enzyme is stabilized by association with a stabilizing agent.

4. The method of claim 3, wherein the stabilizing agent is selected from the group consisting of: polyethylene glycol, a synthetic protein polymer, an Fc fusion, and albumin.

5. The method of claim 1, wherein the human Arginase I enzyme is pegylated.

6. The method of claim 1, wherein the subject has a tumor that exhibits a reduced or inhibited expression of argininosuccinate synthetase, ornithine transcarbamylase, argininosuccinate lyase, or a combination thereof.

7. The method of claim 1, wherein the subject is an animal subject.

8. The method of claim 1, wherein the subject s a human cancer patient.

9. The method of claim 1, wherein the agent is ipilimumab.

10. The method of claim 1, wherein the subject has a tumor selected from the group consisting: a hepatocellular carcinoma, a renal cell carcinoma, a breast cancer, a melanoma, a prostate cancer, a pancreatic cancer, a bladder cancer, a colon carcinoma, a colorectal cancer, a triple negative breast cancer, a Hodgkin's lymphoma, a gastric cancer, a glioblastoma, a Merkel cell carcinoma, a lung carcinoma, a small cell lung cancer, and a non-small cell lung cancer.

11. The method of claim 1, wherein the immuno-oncology agent and the human Arginase I enzyme are administered concurrently.

12. The method of claim 1, wherein the immuno-oncology agent and the human Arginase I enzyme are administered sequentially.

13. The method of claim 1, wherein the human Arginase I enzyme displays a $k_{cat}/K_M$ for the hydrolysis of arginine between 400 mM$^{-1}$ s$^{-1}$ and 4,000 mM$^{-1}$ s$^{-1}$ at pH 7.4 and 37° C.

14. The method of claim 1, wherein the human Arginase enzyme comprises a ratio of cobalt to arginase of from 2 to 3 μg Co/mg arginase.

15. The method of claim 1, wherein the human Arginase I enzyme is produced by contacting an arginase apoenzyme with cobalt or a cobalt ion at a temperature of from 30° C. to 55° C. for a period of from 15 minutes to 60 minutes.

16. A method of treating cancer in a cancer patient comprising administering to said patient a therapeutically effective amount of a pharmaceutical composition comprising a pegylated human Arginase I enzyme comprising a cobalt cofactor and an immune system modulating therapy, wherein the immune system modulating therapy is an immuno-oncology agent selected from the group consisting of: pembrolizumab, ipilimumab, atezolizumab, and nivolumab.

17. The method of claim 16, wherein the pharmaceutical composition comprising the pegylated human Arginase I enzyme comprising the cobalt cofactor and the pharmaceutical composition comprising the immuno-oncology agent are administered concurrently.

18. The method of claim 16, wherein the pharmaceutical composition comprising the human Arginase I enzyme comprising the cobalt cofactor and the pharmaceutical composition comprising the immuno-oncology agent are administered sequentially.

19. The method of claim 16, wherein the therapeutically effective amount of the pegylated human Arginase I enzyme comprising the cobalt cofactor is from about 0.01 mg/kg to about 7.5 mg/kg.

20. The method of claim 16, wherein the therapeutically effective amount of the pegylated human Arginase I enzyme comprising the cobalt cofactor is from about 0.05 mg/kg to about 5 mg/kg.

21. The method of claim 16, wherein the therapeutically, effective amount of the pegylated human Arginase I enzyme comprising cobalt cofactor is from about 0.1 mg/kg to about 5 mg/kg.

22. The method of claim 16, wherein the cancer patient is treated for a hepatocellular carcinoma, a renal cell carcinoma, a breast cancer, a melanoma, a prostate cancer, a pancreatic cancer, a bladder cancer, a colon carcinoma, a colorectal cancer, a triple negative breast cancer, a Hodgkin's lymphoma, a gastric cancer, a glioblastoma, a Merkel cell carcinoma, a lung carcinoma, a small cell lung cancer, or a non-small cell lung cancer.

23. The method of claim 16, wherein the pharmaceutical composition comprising the pegylated human Arginase I enzyme comprising the cobalt cofactor is administered parenterally.

24. The method of claim 16, wherein the pharmaceutical composition comprising the pegylated human Arginase I enzyme comprising the cobalt cofactor is administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

25. The method of claim 16, wherein the pharmaceutical composition is administered intravenously.

26. The method of claim 16, wherein the treatment results in from 50% to 99% reduction in serum arginine in the cancer patient.

27. The method of claim 16, wherein the treatment results in from 90% to 99% reduction of serum arginine in the cancer patient.

28. The method of claim 16, Wherein the treatment results in reduction of serum arginine in the cancer patient to an undetectable level.

* * * * *

UNITED STATES PATENT AND TRADEMARK OFFICE
CERTIFICATE OF CORRECTION

PATENT NO. : 10,729,752 B2  
APPLICATION NO. : 15/699951  
DATED : August 4, 2020  
INVENTOR(S) : David Lowe et al.

Page 1 of 1

It is certified that error appears in the above-identified patent and that said Letters Patent is hereby corrected as shown below:

In the Claims

In Claim 8, Column 27, Line 49, replace "s" with "is".

In Claim 14, Column 28, Line 5, replace "Arginase" with "Arginase I".

In Claim 28, Column 29, Line 9, replace "Wherein" with "wherein".

Signed and Sealed this
Fourth Day of May, 2021

Drew Hirshfeld
*Performing the Functions and Duties of the
Under Secretary of Commerce for Intellectual Property and
Director of the United States Patent and Trademark Office*